United States Patent
Jones et al.

(10) Patent No.: US 6,287,293 B1
(45) Date of Patent: Sep. 11, 2001

(54) METHOD AND APPARATUS FOR LOCATING THE INJECTION POINT OF AN IMPLANTED MEDICAL DEVICE

(75) Inventors: Donald Jones, West Valley; Joseph Barrett, Kaysville; Donald Geer, Sandy, all of UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/382,011

(22) Filed: Sep. 28, 1999

(51) Int. Cl.$^7$ ....................................................... A61K 9/22
(52) U.S. Cl. ........................................ 604/891.1; 604/502
(58) Field of Search .............................. 604/93, 164, 167, 604/49, 891.1, 502, 93.01, 288.01, 288.02, 288.04, 97.03

(56) References Cited

U.S. PATENT DOCUMENTS

| | | |
|---|---|---|
| 3,919,724 | 11/1975 | Sanders et al. . |
| 3,951,147 | 4/1976 | Tucker et al. . |
| 4,202,349 | 5/1980 | Jones . |
| 4,456,011 | 6/1984 | Warnecke . |
| 4,697,595 | 10/1987 | Breyer et al. . |
| 4,760,837 | 8/1988 | Petit . |
| 4,781,685 | 11/1988 | Lehmann et al. . |
| 4,861,341 | 8/1989 | Woodburn . |
| 4,886,501 | 12/1989 | Johnston et al. . |
| 4,966,583 | 10/1990 | Debbas . |
| 5,085,216 | 2/1992 | Henley, Jr. et al. . |
| 5,092,849 | 3/1992 | Sampson . |
| 5,137,529 | * 8/1992 | Watson et al. ..................... 604/891.1 |
| 5,152,753 | * 10/1992 | Laguette et al. ..................... 604/153 |
| 5,201,715 | 4/1993 | Masters . |
| 5,320,100 | 6/1994 | Herweck et al. . |
| 5,328,480 | 7/1994 | Melker et al. . |
| 5,352,204 | 10/1994 | Ensminger . |
| 5,360,407 | * 11/1994 | Leonard et al. ..................... 604/175 |
| 5,405,402 | 4/1995 | Dye et al. . |
| 5,676,146 | 10/1997 | Scarborough . |
| 5,713,858 | 2/1998 | Heruth et al. . |
| 5,718,682 | * 2/1998 | Tucker ..................... 604/93 |
| 5,725,507 | 3/1998 | Petrick . |
| 5,792,116 | * 8/1998 | Berg et al. ..................... 604/202 |
| 5,824,071 | * 10/1998 | Nelson et al. ..................... 623/3 |
| 5,833,654 | * 11/1998 | Powers et al. ..................... 604/93 |
| 5,868,702 | * 2/1999 | Stevens et al. ..................... 604/93 |
| 5,947,953 | * 9/1999 | Ash et al. ..................... 604/508 |
| 6,171,298 | * 1/2001 | Mastuura ..................... 604/891.1 |

* cited by examiner

Primary Examiner—Richard K. Seidel
Assistant Examiner—Kevin C. Sirmons
(74) Attorney, Agent, or Firm—Morrison & Foerster; Todd W. Wight

(57) ABSTRACT

A method and apparatus for locating the injection point of an implanted medical device. In a preferred embodiment, the locating apparatus is in the form of radiopaque rings made of a metallic substance. When these rings are spaced apart at different heights on an implanted medical device, such as a drug port, a stereoscopic effect results from fluoroscopically viewing the device along an axis not parallel to the axis along which the rings are spaced. This effect allows one to readily determine the orientation of the device. This prevents accidental injection of drugs into the hard backside of the drug port.

32 Claims, 3 Drawing Sheets

METHOD AND APPARATUS FOR LOCATING THE INJECTION POINT OF AN IMPLANTED MEDICAL DEVICE

BACKGROUND OF THE INVENTION

1. Field of the Invention

The present invention relates generally to a method for determining the location of implanted medical devices, and more particularly to locators incorporated into a drug port to allow determination of septum orientation prior to injection.

2. Description of Related Art

Medical devices implanted beneath a patient's skin are well known in the art. Many devices require locating systems so that their exact location can be determined using various techniques such as ultrasound and fluoroscopy. There is a wide array of patents utilizing locating techniques for catheters, injection ports and other medical prosthetics. For example, U.S. Pat. No. 4,697,595 to Breyer et al. discloses a locating technique for catheters. A catheter with embedded ultrasonic piezoelectric transducers is used. The transducers connect to electrical leads that relay an electrical signal in response to an ultrasonic beam, thereby pinpointing the position of the catheter tip. Locators have also been used for implantable prosthetic devices.

U.S. Pat. No. 5,405,402 to Dye et al. discloses a radiographic marker incorporated into an implantable prosthesis. The marker comprises a tension coil spring that forms a continuous ring to encircle the prosthetic member. The prosthetic member can then be readily aligned using the radiographic marker.

The present invention relates generally to implantable medical devices and more specifically to devices containing self-sealing injection sites or ports. Devices such as tissue expanders and drug delivery access ports feature self-sealing septa so the devices can be filled periodically by needle injection. It is vital to accurately determine the location of such septa before injecting a drug that could cause considerable damage if inadvertently injected into the peripheral tissues of the patient. Many patents have attempted to solve this vexing problem. U.S. Pat. No. 4,781,685 to Lehmann et al. addresses the problem by providing an external signaling device which signals when a needle is positioned correctly inside of an implantable drug dispensing capsule. U.S. Pat. No. 5,137,529 to Watson et al. addresses the locating problem by placing a barium impregnated silicone tube over an outlet connector to provide a radiopaque indicator of the location of the injection port. U.S. Pat. No. 5,725,507 to Petrick also uses barium sulfate to provide a radiopaque member for location of an injection site. Finally, U.S. Pat. No. 5,201,715 to Masters discloses an additional way to locate an injection port by using implantable devices having distinct ultrasonic echographic signatures. The ultrasonic targets are placed below the septum within the injection port, and when an ultrasonic source irradiates the target, multiple reflections occur from the targets.

Unfortunately, it is sometimes very difficult to determine the precise location and orientation of injection ports. The prior art discussed above, while addressing the problem of determining the location of an injection site, does not really solve the problem of also determining orientation of the device within the body. While locating the injection port itself is important, mistakes can be made despite using the above-mentioned two-dimensional location techniques. For example, although the injection site in Petrick can seemingly be located by its radiopaque marker, the orientation of the drug port is not revealed. Thus, if the port is actually inverted (i.e., the septum faces away from the skin surface), the needle could be pushed into the back of the port causing numerous problems ranging from puncture of the port to injection of the drug into the peripheral tissues. Additionally, if the back of the port is sufficiently hard, a portion of the needle could break off inside the body causing infection and other complications. In either case, invasive surgery is necessary to remove the damaged items, opening up the possibility for even further complications.

The prior art mentioned also exhibits certain other shortcomings. In particular, although Watson attempts to address the problem of orientation, the placement of the barium-impregnated tube doesn't reveal whether the port is correctly oriented for injection or whether it has "flipped" over. A problem with Lehmann et al. is the device's complexity and the fact that although the device signals when the needle is in the correct position, it does nothing to aid the physician in locating the port and also does not reveal orientation in advance of the attempted injection. Masters describes a method to locate the center of an injection port by providing a locator that produces ultrasonic signatures. This method does not appear to reveal septum orientation.

Thus, it would be desirable to create an implanted drug port with a self-sealing injection site equipped with means for determining location, not only in terms of position inside of the body but also in terms of orientation at that site. In addition, it would be desirable to provide a simple, easy and inexpensive way to create this apparatus. It would be further desirable to provide this apparatus so that current medical techniques for viewing an implanted device could be employed. Further, the locating means should not interfere with widely used diagnostic imaging techniques such as MRI (Magnetic Resonance Imaging).

SUMMARY OF THE INVENTION

Accordingly, it is an object of the present invention to provide radiopaque indicators to be placed on or in an implantable medical device so that the device can be viewed fluoroscopically.

Another object of the invention is to provide multiple locators to be placed on an implantable drug port at varying distance from the skin surface (depths) so that the device can be viewed stereoscopically, as a three-dimensional object inside the body.

A further object of the invention is to provide locators that indicate the orientation of an implanted medical device as well as the orientation of particular features of the medical device.

Yet another object of the invention is to provide a way to locate an implanted medical device and determine its orientation which requires little or no maintenance.

A further object is to provide locators that do not interfere with MRI or similar imaging techniques.

These and other objectives of the present invention are achieved by providing multiple rings or locators of other shapes and types for incorporation into an implantable medical device. The locators can be radiopaque and are positioned, for example, inside of a drug port at varying levels so that a significant difference in depth is created between the locators. Thus, a three-dimensional or stereoscopic effect is created when the drug port is viewed fluoroscopically after implantation beneath the skin. The depth aspect of the invention is enhanced by the fact that the locators can be of varying diameters to accommodate the shape of the drug port. In addition, the locator on the bottom of the port preferably has a discontinuity or other indicator that is aligned with the axis of the stem to be used to identify the orientation of the port stem. With the above-mentioned characteristics, the rings or other types of locators enable a physician to determine the orientation of the port when viewed fluoroscopically. Since a type of stereoscopy is involved, the physician can decide whether or not the drug port has turned over while inside the body. This prevents the injection into the incorrect side of the device and the resulting complications.

BRIEF DESCRIPTION OF THE DRAWINGS

These and other objects, features and advantages of the present invention will become more apparent to those skilled in the art when taken with reference to the following more detailed description of the preferred embodiments of the invention in conjunction with the accompanying drawings.

In the detailed description that follows, it should be appreciated that like reference numerals are used to describe like elements illustrated in one or more of the figures.

DETAILED DESCRIPTION OF THE PREFERRED EMBODIMENTS

The present invention satisfies the need for a way to determine the location and orientation of an implanted drug port in an inexpensive way by providing a method and apparatus for incorporating locators or indicators into the drug port at various levels which allow determination of orientation when viewed from the side.

Figure 1:
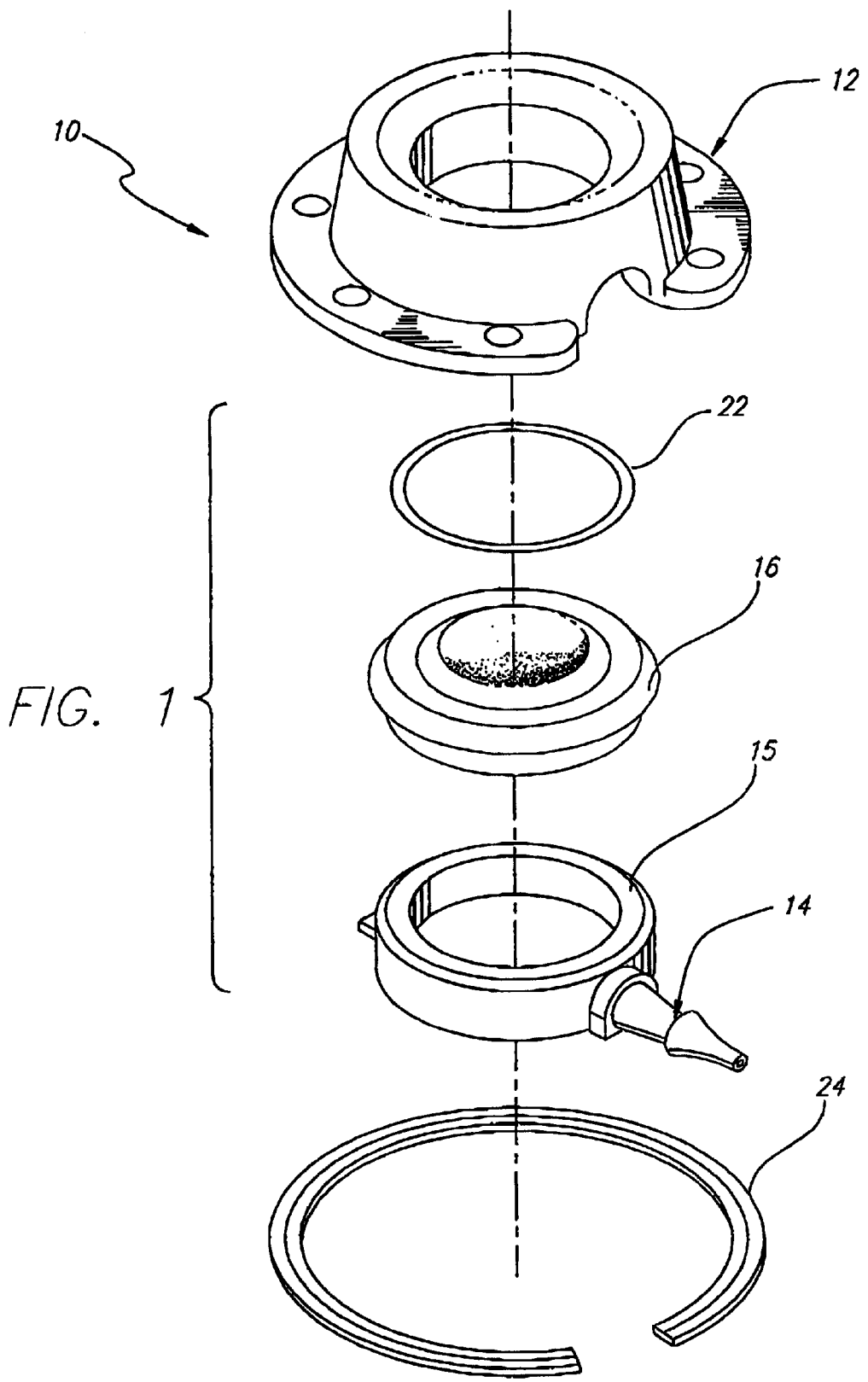
FIG. 1 is an exploded view of locator rings as incorporated into a drug port.
Figure 2:
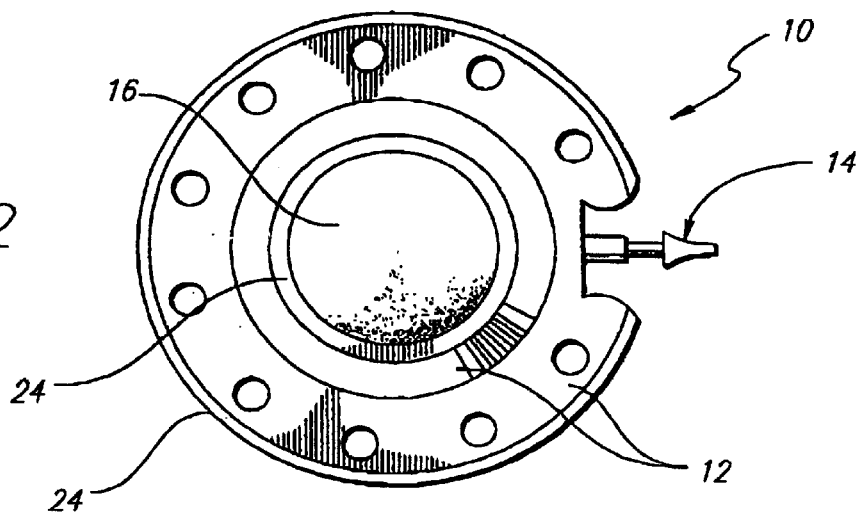
FIG. 2 is a top view of a drug port.

Turning now to FIGS. 1 and 2, an exploded view and a top view of drug port 10 is shown respectively. The drug port 10 comprises a low profile port top 12, a low profile port base 15 with a port stem 14, and a low profile port septum 16. The locators in this first embodiment are rings, which are incorporated into the drug port 10. A first locator ring 22 is placed above the port septum 16 to fit underneath the upper lip of the port top 12. A second locator ring 24 is fitted beneath the bottom lip of the port top 12 and has a discontinuity 25 disposed to indicate the location of the port stem 14. The locator rings 22 and 24 of the first embodiment are made from a radiopaque material such as gold, platinum, tungsten, tantalum, a barium compound, a medical grade titanium or stainless steel and can be manufactured by either machining, stamping or extruding. It will be appreciated by one of ordinary skill in the art of medical imaging that continuous or substantially continuous metallic rings as shown in the drawings may interfere with MRI because currents and associated magnetic fields are set up within the conductors. Therefore it is preferable to extrude the rings from a plastic resin paste containing powdered radiopaque metals or other materials such as barium sulfate, thereby limiting or eliminating induced currents. Alternatively, continuous or discontinuous depressions within the drug port 10 can be filled with such a resin that is then polymerized in place or with metal pellets, etc.

The first locator ring 22 can be inserted during the welding process when the port top 12, the port septum 16 and the port base 15 are joined together. The second locator ring 24 can be placed on the bottom of port top 12 during an over-molding process when the bottom of drug port 10 is encapsulated in a silicone rubber material. Alternatively, the locator rings 22 and 24 can be ultrasonically welded to the device, press-fitted to the device, or attached with adhesives. These fabrication methods are for example only and do not in any way limit the invention. In an alternate embodiment, for example, the locators could be painted onto the drug port with radiopaque paint or formed by injection into holes or grooves of resin (e.g. silicone polymer) and powdered radiopaque material or pellets as mentioned above.

Figure 3:
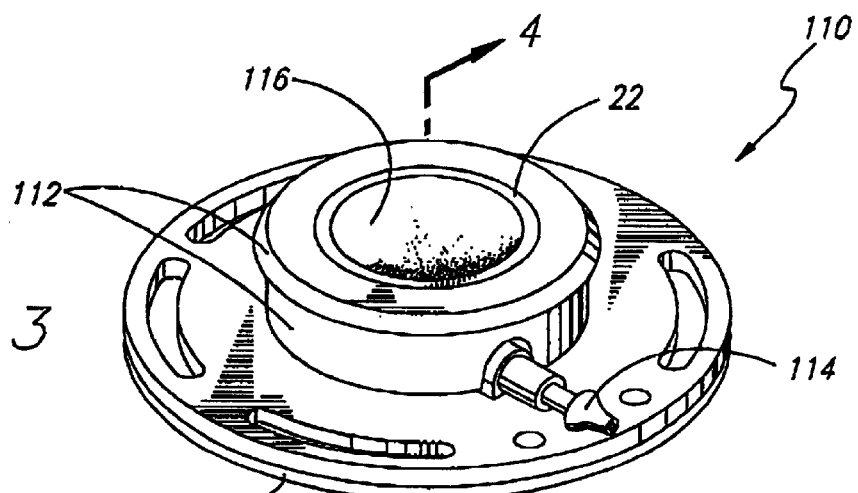
FIG. 3 is a side perspective view of the drug port of FIG. 2.

Referring now to FIG. 3, an alternative embodiment drug port 110 is shown from the side in perspective. The drug port 110 comprises a low profile port shell 112, a port stem 114, and a port septum 116. As in FIGS. 1 and 2, locator rings 22 and 24 are incorporated into the drug port 110 above the port septum 116 underneath the upper lip of port shell 112, and underneath the bottom lip of port shell 112 respectively.

Figure 4:
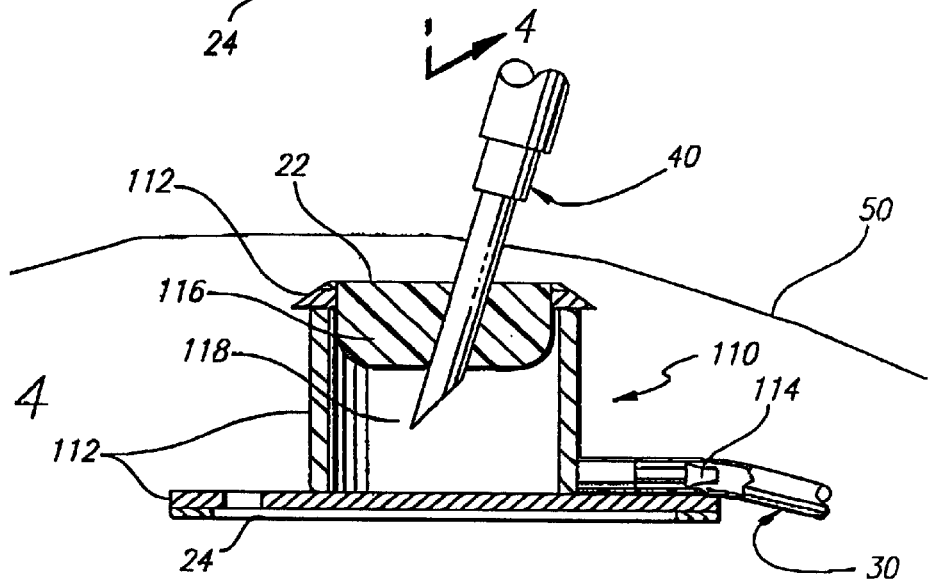
FIG. 4 is a cross-sectional view of the drug port of FIG. 2 as it is being filled by injection.
Figure 5A:
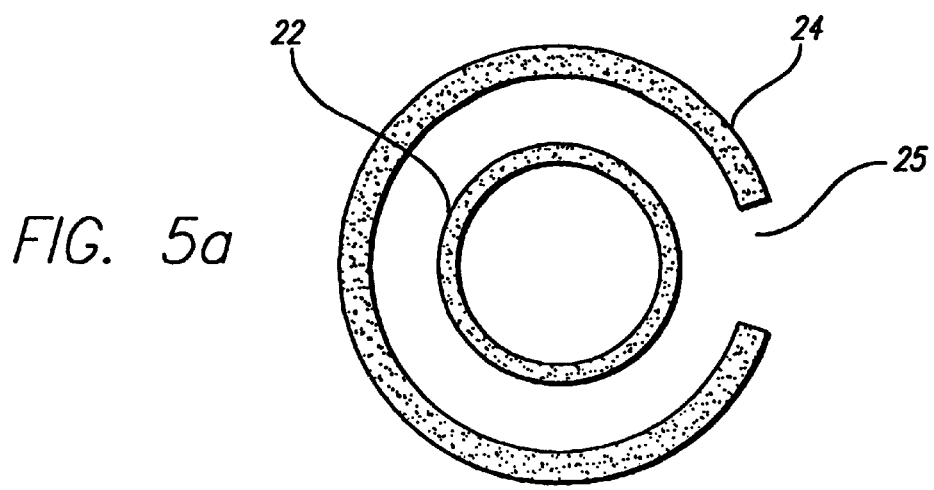
FIG. 5a is a view of an implanted drug port with locators incorporated as viewed fluoroscopically from the top.
Figure 5B:
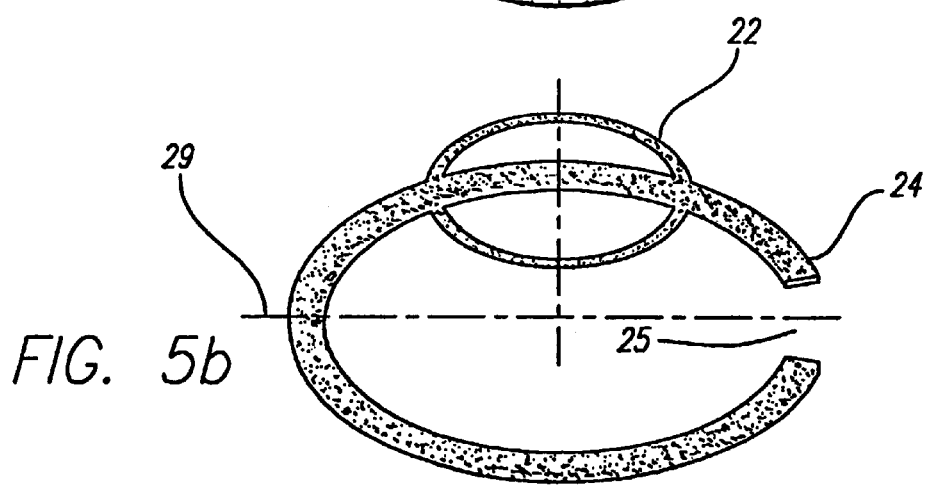
FIG. 5b is a view of an upright implanted drug port with locators incorporated as viewed fluoroscopically from the side.
Figure 5C:
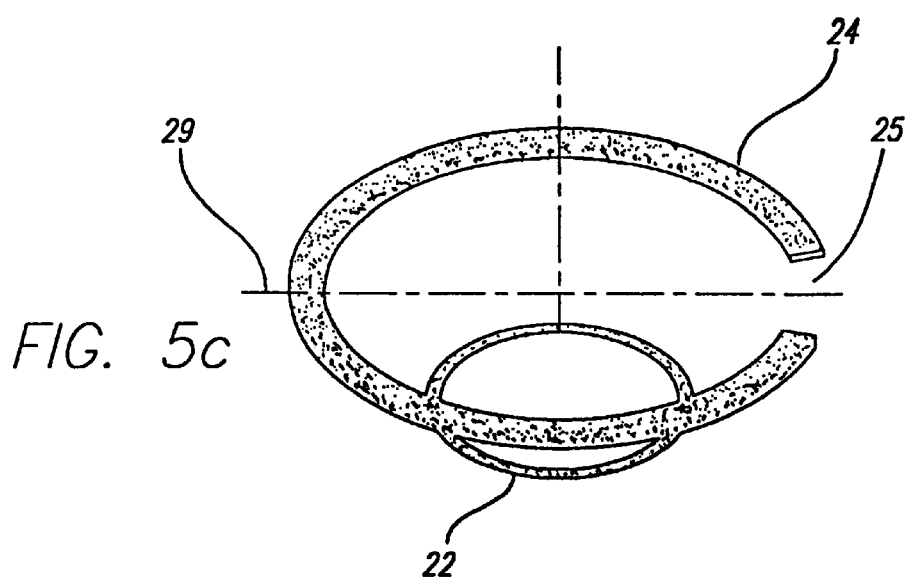
FIG. 5c is a view of an upside down implanted drug port with locators incorporated as viewed fluoroscopically from the side.

FIG. 4 shows a cross-sectional view of the drug port 110 implanted beneath skin surface 50. The drug port 110 is shown being penetrated by needle 40 for injection of a liquid drug into the port 110. A physician first views a patient with the implanted drug port fluoroscopically to determine the location of the drug port 110. Once the drug port 110 is located, its orientation must be discerned. FIG. 5 demonstrates the advantage of the present invention in determining the orientation of any drug port. In FIG. 5a, a drug port is viewed fluoroscopically from above. Although the location of a port stem is apparent because of the discontinuity in the second locator ring 24 or because of a radiopaque port stem 114 (not shown), locator rings 22 and 24 do not reveal the orientation (e.g., whether it is upside down) of the drug port, thereby allowing the backside injection problems discussed above. When viewed at an angle from the side, however, the distance between the rings provides a three-dimensional effect in which the locators overlap thus enabling the physician to determine the orientation of the drug port. FIG. 5b shows an off-axis view of a drug port in an upright position with the first locator ring 22 superimposed over the "upper" portion (in reference to the line 29 which bisects the discontinuity 25) of the second locator ring 24. In this position, the port is positioned for injection, and the process can be carried out as shown in FIG. 4. FIG. 5c shows a drug port in an inverted position with the first locator ring 22 superimposed on the "lower" portion of the second locator ring 24. In this orientation, the drug port must be "flipped over" before injection of the drug can safely take place. In FIGS. 5b and 5c the images are intended to represent radiographs wherein the stippled areas represent shadows thrown by radiopaque materials. The x-ray beam forming the images comes from the approximate position of the reader viewing these figures. Referring to FIG. 4, needle 40 is inserted through the skin surface 50 and into drug port 110 through the self-sealing septum 116 and into the inner chamber 118 of port shell 112. The drug is released into the inner chamber 118 where it is slowly administered to a predetermined area through the catheter 30.

Two factors must be met for this locator system to operate. First the indicators must be spaced apart along a first axis that bears a known relationship to the implanted device.

Most preferably this first axis should be parallel to the axis defining the height of the device. When the device is imaged along an axis oblique to this first axis, the indicators will overlap (as shown in FIGS. 5b and 5c). If the second factor is met, namely that the indicators can be distinguished from each other in the image, then the image overlap will define the orientation of the device. If the image of the lower indicator or locator 24 is bisected by a line 29 drawn at right angles to the imaging axis (essentially the line of sight of the reader viewing the figures), the image of the upper indicator or locator 22 will appear above this line 29 if the device is oriented "upright"(i.e., the correct orientation for injection into the device) and below this line 29 if the device is oriented "upside-down." In summary, for the locating system to operate the locators must be distinguishable in the image (i.e., the upper locator 22 must be distinguishable from the lower locator 24) and the locators must be spaced apart along an axis more or less parallel to the height of the device. The embodiments shown use ring-shaped locators. This shape is preferred because of its simplicity but locators of other shapes are operable as long as the constraints explained above are met. Here the locators are distinguished either by the presence of a discontinuity in the "lower" locator or by the presence of a radiopaque port stem 114 in close proximity to the lower "locator". Alternatively, the two locators can have distinguishable shaped or markings (e.g., holes or projections).

A second embodiment of the present invention, as mentioned above, employs locators in the form of radiopaque paint or radiopaque material in the form of semi-liquid resin that is applied in a liquid or plastic state. The radiopaque liquid is painted onto the drug ports at separate spaced apart locations of different diameters or injected into holes or grooves to establish a spatial distance as well as to establish exact orientation. In this embodiment, the material can be applied in a circular pattern around the outer edge of the drug port or in any other pattern that would accomplish the same objective. For example, the lower indicator, shown in FIG. 1 as locator ring 24, could be applied to the bottom of port top 12 in the shape of an arrow with the point indicating the location of port stem 114. Of course, it is important that the second locator ring 24 cover a sufficient area that a fluoroscopic side view readily reveals the orientation. If the second locator 24 were limited to a small arrow the positional differences exemplified by FIGS. 5b and 5c might be difficult to discern. As explained above, the use of plastic radiopaque material avoids continuous electrical conductors that may interfere with MRI.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself The definitions of the words or elements of the following claims are, therefore, defined in this specification to include not only the combination of elements which are literally set forth, but all equivalent structure, material or acts for performing substantially the same function in substantially the same way to obtain substantially the same result.

Having thus described preferred embodiments of the method and apparatus for locating an implanted medical device, it should be apparent to those skilled in the art that certain advantages of the within system have been achieved. It should also be appreciated that various modifications, adaptations, and alternative embodiments thereof may be made within the scope and spirit of the present invention by those having ordinary skill in the art. For example, locators to determine position and orientation of a drug port have been illustrated, but it should be apparent that the inventive concepts described above would be equally applicable to other implantable medical devices. In addition, while the use of radiopaque rings or radiopaque paint to locate a drug port has been discussed, other radiopaque or similar performing material could be used. The invention is further defined by the following claims.

We claim:

1. An implantable drug port, comprising:
    a low profile housing, comprising a port top and a port base, wherein the low profile port base further comprises a low profile port stem;
    a septum disposed within the housing, wherein a lumen is defined within the housing beneath the septum and accessible through the septum; and
    at least two indicators disposed on the housing, spaced apart along an axis of the housing.

2. The implantable drug port according to claim 1, wherein said indicators are formed from radiopaque material.

3. The implantable drug port according to claim 2, wherein said radiopaque material further comprises radiopaque paint.

4. The implantable drug port according to claim 2, wherein the radiopaque material further comprises radiopaque plastic material, wherein a lower ring is applied to a bottom portion of the port top and an upper ring is applied to an upper portion of the port top.

5. The implantable drug port according to claim 4, wherein the low profile housing is encapsulated in a silicone rubber material.

6. The implantable drug port according to claim 4, wherein the lower ring has a discontinuity such that the discontinuity is aligned with the port stem.

7. The implantable drug port according to claim 1, wherein said indicators comprise a plurality of rings.

8. The implantable drug port according to claim 7, wherein said plurality of rings further comprises a lower ring of a first diameter disposed near a bottom of said drug port and an upper ring of a second diameter, different from said first diameter, disposed near a top of said drug port.

9. The implantable drug port according to claim 8, wherein said lower ring is interrupted creating a discontinuity.

10. The implantable drug port according to claim 7, wherein said plurality of rings are comprised of a metal selected from the group consisting of stainless steel, gold, platinum, tungsten tantalum and titanium.

11. The implantable drug port according to claim 7, wherein said plurality of rings are comprised of a resin and a powdered material selected from the group consisting of stainless steel, gold, platinum, tungsten tantalum, titanium and a barium compound.

12. The implantable drug port according to claim 1, wherein the indicators comprise a lower locator ring and an upper locator ring, wherein the lower locator ring is interrupted creating a discontinuity, and is disposed at a bottom of said low profile housing such that the discontinuity is aligned with the port stem, and wherein the upper locator ring is placed between the septum and the port top.

13. The implantable drug port according to claim 12, wherein the low profile housing is encapsulated with a silicone rubber material.

14. The implantable drug port according to claim 1, further comprising a radiopaque catheter connected to the port stem.

15. The implantable drug port according to claim 1, wherein the indicators are formed to be distinguishable from each other by imaging when said drug port is implanted.

16. A method for determining an orientation of an implantable drug port to assist in guiding a needle into the port, wherein the implantable drug port comprises a non-inflatable housing having a first and second side, a septum disposed within the housing and a first and second indicator spaced apart along a first axis of the housing comprising the steps of:

locating the implanted non-inflatable housing;

imaging the housing along a second axis not parallel to the first axis; and determining the orientation of the housing with respect to the first and second sides.

17. The method according to claim 16, wherein said indicators comprise radiopaque material.

18. The method according to claim 17, wherein said radiopaque material is selected from the group consisting of gold, platinum, tungsten, tantalum, stainless steel, titanium and barium compounds.

19. The method according to claim 17, wherein said radiopaque material further comprises radiopaque plastic material.

20. The method according to claim 16, wherein at least one of said indicators is ring shaped.

21. The method according to claim 20, wherein said ring shaped indicator is interrupted creating a discontinuity.

22. The method according to claim 20, wherein a radiopaque catheter is disposed to bisect said ring shaped indicator.

23. A method for guiding a needle into an implantable drug port, comprising the steps of:

providing a drug port comprising a non-inflatable housing, a septum disposed within the housing and a first and second indicator spaced apart along a first axis of the housing, wherein the indicators are distinguishable, one from the other, by an imaging technique;

implanting the drug port with the first axis normal to a patient's skin surface;

employing the imaging technique to image the drug port along a second axis not parallel to the first axis;

determining the orientation of the drug port based on an imaged spatial relationship of the first indicator to the second indicator; and inserting the needle into the septum at a location where the septum is accessible.

24. An implantable drug port, comprising:

a housing;

a septum disposed within the housing, wherein a lumen is defined within the housing beneath the septum and accessible through the septum; and indicators associated with the housing, comprising a lower locator ring and an upper locator ring, wherein the rings are spaced apart along an axis of the housing, and wherein at least one of the rings is interrupted creating a discontinuity.

25. The implantable drug port according to claim 24, wherein the rings are formed from radiopaque material.

26. The implantable drug port according to claim 25, wherein the radiopaque material is a metal selected from the group consisting of stainless steel, gold, platinum, tungsten tantalum and titanium.

27. The implantable drug port according to claim 25, wherein the radiopaque material is a resin and a powdered material selected from the group consisting of stainless steel, gold, platinum, tungsten tantalum, titanium and a barium compound.

28. The implantable drug port according to claim 25, wherein the radiopaque material further comprises radiopaque paint.

29. The implantable drug port according to claim 25, wherein the radiopaque material further comprises radiopaque plastic material.

30. The implantable drug port according to claim 24, wherein the housing is encapsulated with a silicone rubber material.

31. The implantable drug port according to claim 24, further comprising a port stem, wherein the discontinuity is aligned therewith.

32. The implantable drug port according to claim 31, further comprising a radiopaque catheter, wherein the radiopaque catheter is connected to the port stem.

* * * * *